(12) United States Patent
King

(10) Patent No.: US 8,569,536 B2
(45) Date of Patent: *Oct. 29, 2013

(54) C-NITROSO-DERIVED NITROXYL DONORS

(75) Inventor: S. Bruce King, Walnut Cove, NC (US)

(73) Assignee: Wake Forest University Health Sciences, Winston-Salem, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 13/589,422

(22) Filed: Aug. 20, 2012

(65) Prior Publication Data

US 2013/0040919 A1    Feb. 14, 2013

Related U.S. Application Data

(63) Continuation of application No. 13/177,036, filed on Jul. 6, 2011, now Pat. No. 8,269,034, which is a continuation of application No. 12/710,778, filed on Feb. 23, 2010, now Pat. No. 7,989,652, which is a continuation of application No. 12/293,374, filed as application No. PCT/US2007/009160 on Apr. 13, 2007, now Pat. No. 7,696,373.

(60) Provisional application No. 60/744,792, filed on Apr. 13, 2006.

(51) Int. Cl.
*C07C 69/76* (2006.01)
*C07C 207/00* (2006.01)
*A61K 31/235* (2006.01)
*A61K 31/04* (2006.01)

(52) U.S. Cl.
USPC ........... 560/105; 560/109; 568/949; 514/533; 514/166; 514/741

(58) Field of Classification Search
USPC ............ 560/105, 109; 568/949; 514/533, 741
See application file for complete search history.

(56) References Cited

U.S. PATENT DOCUMENTS 6,946,441 B2 *  9/2005  Long et al. ................... 514/15.6

OTHER PUBLICATIONS

Rehse et al. Azodioxides Activated by Electron Acceptors in Geminal or Vicinal Position, Arch. Pharm. Pharm. Med. Chem., 1998, vol. 331, 104-110.*
Zhutov et al. p-Bromo (diacetoxyiodo) benzene, and Efficient Oxidant for Conversion of Oximes into Nitroso Compounds. Russian Journal of Organic Chemistry, 2003, vol. 39 (11), 1672-1673.*

* cited by examiner

*Primary Examiner* — Sikarl Witherspoon
(74) *Attorney, Agent, or Firm* — Myers Bigel Sibley & Sajovec, P.A.

(57) ABSTRACT

Active compounds of Formula I are described:

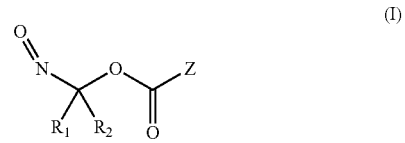

wherein: $R_1$ and $R_2$ are each independently C1-C4 alkyl; or $R_1$ and $R_2$ together form a C2-C7 alkylene chain; and Z is a non-steroidal anti-inflammatory drug (NSAID); along with pharmaceutically acceptable salts and prodrug thereof, and methods of using the same.

10 Claims, No Drawings

C-NITROSO-DERIVED NITROXYL DONORS

RELATED APPLICATIONS

This application claims priority to and is a continuation of U.S. patent application Ser. No. 13/177,036, filed on Jul. 6, 2011, now U.S. Pat. No. 8,269,034 now allowed, which is a continuation of U.S. patent application Ser. No. 12/710,778, filed on Feb. 23, 2010, now U.S. Pat. No. 7,989,652, which is a continuation of U.S. patent application Ser. No. 12/293,374, filed Oct. 1, 2008, now U.S. Pat. No. 7,696,373, which is a national phase application of PCT Application PCT/US2007/009160, filed Apr. 13, 2007, and published in English on Oct. 25, 2007, as International Publication No. WO 2007/120839, and which claims the benefit under 35 U.S.C. §119(e) of U.S. Provisional Patent Application Ser. No. 60/744,792, filed Apr. 13, 2006, the disclosure of each of which is incorporated herein by reference in its entirety.

STATEMENT OF FEDERAL SUPPORT

This invention was made with Government support under contract number HL62198 awarded by the National Institutes of Health. The Government has certain rights in the invention.

FIELD OF THE INVENTION

The present invention concerns C-nitroso derived nitroxyl donors, methods of making and using the same, and pharmaceutical formulations thereof.

BACKGROUND OF THE INVENTION

NO-donors have been suggested to have antithrombotic and vasodilating activity. K. Rehse and M. Herpel, *Arch. Pharm. Pharm Med. Chem.* 331, 104-110 (1998) describe on page 104 the following compounds:

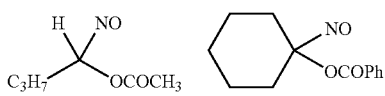

additional compounds are described on page 106 in Table 1 therein.

More recently, V. Daineko et al., *Russian Journal of Organic Chemistry*, 38, 1431-1433 (2002) describe compounds of the formula:

where (for I) R is Me, or (for II) RR is $(CH_2)_5$. See also E. Zhutov et al., *Russian Journal of Organic Chemistry*, 39, 1672-1673 (2003)

SUMMARY OF THE INVENTION

A first aspect of the invention is a compound (sometimes referred to as "active compounds" herein) of Formula I:

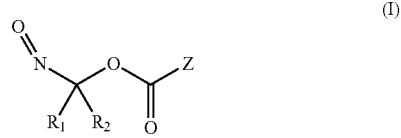

wherein:
$R_1$ and $R_2$ are each independently C1-C4 alkyl;
or $R_1$ and $R_2$ together form a C2-C7 alkylene chain; and
Z is a non-steroidal anti-inflammatory drug (NSAID);
or a pharmaceutically acceptable salt or prodrug thereof. A particular example is:

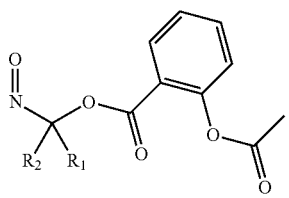

or a pharmaceutically acceptable salt or prodrug thereof.
A further aspect of the present invention is an compound (sometimes referred to as an "active compound" herein) of Formula (III):

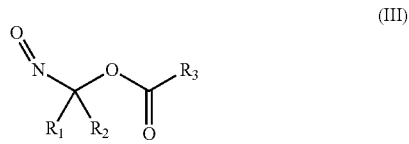

wherein:
$R_1$ and $R_2$ are each independently C1-C4 alkyl;
or $R_1$ and $R_2$ together form a C2-C7 alkylene chain; and
$R_3$ is C1-C5 alkyl, haloalkyl or aryl,
or a pharmaceutically acceptable salt or prodrug thereof.
A further aspect of the invention is a pharmaceutical composition (e.g., for treating congestive heart failure) comprising a compound or active compound as described herein in a pharmaceutically acceptable carrier.
A further aspect of the invention is a method of treating a cardiovascular disorder such as congestive heart failure in a subject in need thereof, comprising administering said subject a treatment-effective amount of a compound or active compound as described herein. Optionally, the method may include concurrently administering a beta blocker to the subject in a treatment-effective amount.
A further aspect of the present invention is a method of treating gastrointestinal side effects associated with NSAID treatment in a subject in need thereof, comprising administering said subject a treatment-effective amount of an active compound as described herein.

DETAILED DESCRIPTION OF THE PREFERRED EMBODIMENTS

The present invention is primarily concerned with the treatment of human subjects, but the invention may also be carried out on animal subjects, particularly mammalian subjects such as mice, rats, dogs, cats, livestock and horses for veterinary purposes.

"Alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. Alkyl may be substituted or unsubstituted unless specified otherwise and where substituted may be substituted one or more (e.g., one, two or three times) with another group such as hydroxy, halo (fluoro, chloro, bromo, iodo), nitro, amino, or the like.

"Haloalkyl" as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylene" as used herein refers to a difunctional alkyl group where "alkyl" is as defined above. Examples include, but are not limited to, —CH$_2$CH$_2$CH$_2$CH$_2$—, —CH$_2$CH$_2$CH$_2$CH$_2$CH$_2$—, and —CH$_2$CH$_2$CH$_2$CH$_2$CH$_2$CH$_2$—.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

The term "treat" as used herein refers to any type of treatment that imparts a benefit to a patient afflicted with a disease, including improvement in the condition of the patient (e.g., in one or more symptoms), delay in the progression of the disease, etc.

The term "pharmaceutically acceptable" as used herein means that the compound or composition is suitable for administration to a subject to achieve the treatments described herein, without unduly deleterious side effects in light of the severity of the disease and necessity of the treatment.

Active compounds of the present invention may optionally be administered in conjunction with other compounds useful in the treatment of cardiovascular disease. The other compounds may optionally be administered concurrently. As used herein, the word "concurrently" means sufficiently close in time to produce a combined effect (that is, concurrently may be simultaneously, or it may be two or more events occurring within a short time period before or after each other).

As used herein, the administration of two or more compounds "in combination" means that the two compounds are administered closely enough in time that the presence of one alters the biological effects of the other. The two compounds may be administered simultaneously (i.e., concurrently) or sequentially. Simultaneous administration may be carried out by mixing the compounds prior to administration, or by administering the compounds at the same point in time but at different anatomic sites or using different routes of administration.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. Nos. 6,680,324 and 6,680,322.

"Non-steroidal Antiinflammatory Drugs" (NSAID) are known in both conjugated and unconjugated form. See, e.g., U.S. Pat. Nos. 6,355,666 and 6,306,842. Suitable examples include, but are not limited to, aspirin, indomethacin, ibuprofen, fenoprofen, sulindac, naproxen, tolmetin, mefanamic acid, mefclofenamic acid, etc.

"Beta blockers" as used herein are known. See, e.g., U.S. Pat. Nos. 7,005,425 and 6,756,408. Examples include, but are not limited to atenolol, pindolol, esmolol, propranolol, metoprolol, etc.

"Cardiovascular disease" as used herein includes, but is not limited to, thrombosis, congestive heart failure, vasoconstriction, cardiac hypertrophy, arrhythmia, heart attack, hypertension, etc.

"Congestive heart failure" as described herein may be due to any cause, including but not limited to coronary artery disease, myocardial infarction, high blood pressure, heart valve disease, congenital heart defects, endocarditis, myocarditis, or any combination thereof.

The disclosures of all United States patent references cited herein are incorporated herein by reference in their entirety.

1. Active Compounds.

Active compounds of the present invention are, in general, compounds of Formula I:

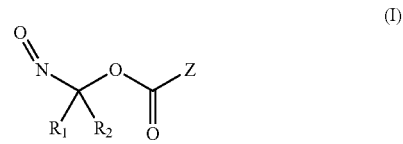

wherein:

R₁ and R₂ are each independently C1-C4 alkyl;

or R₁ and R₂ together form a C2-C7 alkylene chain; and

Z is a non-steroidal anti-inflammatory drug;

and pharmaceutically acceptable salts and prodrugs thereof.

In other embodiments, active compounds of the present invention are compounds of Formula (III):

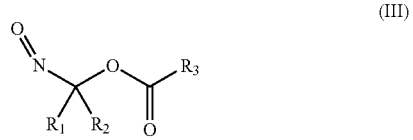

wherein:

R₁ and R₂ are each independently C1-C4 alkyl;

or R₁ and R₂ together form a C2-C7 alkylene chain; and

R₃ is C1-C5 alkyl, haloalkyl or aryl, or a pharmaceutically acceptable salt or prodrug thereof.

Compounds of Formula I or III may be made in accordance with the techniques described herein, or variations thereof that will be apparent to those skilled in the art based upon the instant disclosure. In general, compounds of Formula I of the invention may be produced by reacting a compound of Formula II:

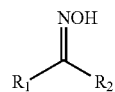

wherein $R_1$ and $R_2$ are as given in connection with formula I above, with a NSAID (preferably a NSAID containing a carboxylic acid group) in the presence of an oxidant and an acid to produce the compound of Formula I. Alternatively, the acid can be substituted by using excess of NSAID. Reaction conditions are not critical. The reaction may be carried out in any suitable organic solvent such as methylene chloride, chloroform, acetic acid, ethyl acetate, diethyl ether, tetrahydrofuran, benzene, or toluene. Reaction temperature can vary from 0° C. to 30° C. Common oxidants of oximes may be used to carry out this reaction such as lead tetraacetate (LTA), (diacyloxyiodo) benzenes, periodates, Dess-Martine perodinane or Swern conditions in the presence of carboxylic acid. Particularly, the method of using (diacyloxyiodo) benzenes to produce acyloxy nitroso compounds has been reported in Zhutov, et. al. Russian Journal of Organic Chem. 2003, 39, 1672-1673 and Calvet, et. al., Organic Letters, 2004, 6, 2449. Additionally, other (diacyloxyiodo) benzenes may be also be used in the reaction. When periodates, especially sodium periodate, is used in the reaction, water or alcohol may be used as a reaction solvent.

An alternative method to prepare the acyloxy nitroso compounds is acylation of the anion of a nitro compound followed by a [3, 2] sigmatropic rearrangement, which is described in Danieko, V. I., Russ. J. Org. Chem. 2002, 38, 1431-1433.

Examples of compounds of the present invention include, but are not limited to, those conjugates shown adjacent the corresponding NSAID as set forth below:

| NSAID | Corresponding Conjugate |
|---|---|
| aspirin | |
| ibuprofen | |
| fenoprofen | |

-continued
| NSAID | Corresponding Conjugate |
|---|---|
| | |
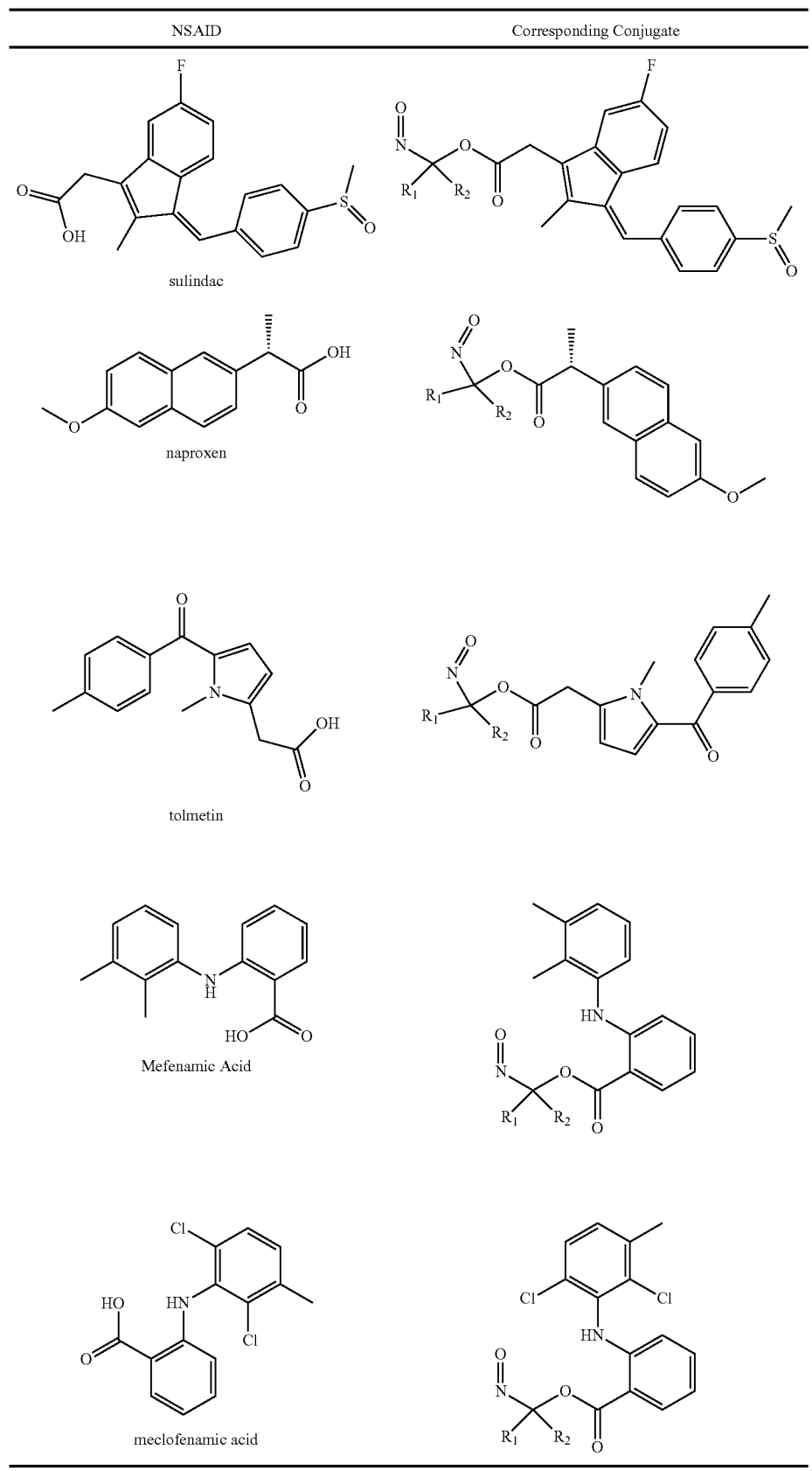
wherein $R_1$ and $R_2$ are as given above.

Examples of compounds of Formula III include, but are not limited to:

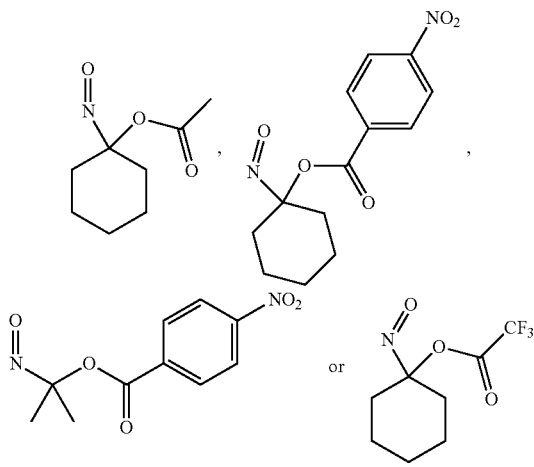

The active compounds disclosed herein can, as noted above, be prepared in the form of their pharmaceutically acceptable salts or prodrugs. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene-disulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Pharmaceutical Formulations.

The active compounds described above may be formulated for administration in a pharmaceutical carrier in accordance with known techniques. See, e.g., Remington, *The Science And Practice of Pharmacy* (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

Preferred routes of parenteral administration include oral, transdermal, and parenteral injection.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. Typically, a dosage from about 0.5 mg/kg to 5 mg/kg may be employed for intramuscular injection. Preferred dosages are 1 µmol/kg to 50 µmol/kg, and more preferably 22 µmol/kg and 33 µmol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the infection.

4. Combination Treatments.

In another embodiment, it is envisioned to use an active compound of the invention in combination with other therapeutic modalities, in like manner as described in U.S. Pat. No. 6,946,441 to Long et al. Thus, in addition to the therapies described above, one may also provide to the patient more "standard" pharmaceutical cardiac therapies. Examples of standard therapies include, without limitation, so-called "beta blockers," anti-hypertensives, cardiotonics, anti-thrombotics, vasodilators, hormone antagonists, iontropes, diuretics, endothelin antagonists, calcium channel blockers, phosphodiesterase inhibitors, ACE inhibitors, angiotensin type 2 antagonists and cytokine blockers/inhibitors.

Combinations may be achieved by contacting cardiac cells with a single composition or pharmacological formulation that includes both agents, or by contacting the cell with two distinct compositions or formulations, at the same time, wherein one composition includes the expression construct and the other includes the agent. Alternatively, the active compound of the invention may precede or follow administration of the other agent by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either an active compound of the invention, or the other agent will be desired. In this regard, various combinations may be employed. By way of illustration, where the active compound is "A" and the other agent is "B", the following permutations based on 3 and 4 total administrations are exemplary:

| | | | | | | | |
|---|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Other combinations are likewise contemplated.

The present invention is explained in great detail in the following non-limiting Examples.

EXAMPLE 1

1-Acetoxy-1-nitrosocyclohexane

A solution of cyclohexanone oxime (5.46 g, 48.25 mmol) in methylene chloride (50 mL) was added dropwise with stirring to a solution of LTA (21.39 g, 48.25 mmol) in methylene chloride (100 mL) at 0° C. A blue color gradually appeared with the addition of the oxime. After 1 h at 0° C., the reaction mixture was warmed to room temperature. After 2 h at room temperature, water (30 mL) was added and the organic layer was extracted with water (2×30 mL) and saturated sodium bicarbonate solution (2×30 mL). The organic layer was dried over $Na_2SO_4$, the solvent evaporated and the residue purified by column chromatography to give 1-Acetoxy-1-nitrosocyclohexane as a bright blue liquid (52% yield): $R_f$ 0.68 (pentane/ethyl acetate=20:1); $^1$H NMR (300 MHz, Benzene-$d_6$) δ 1.1-1.9 (m, 13H); $^{13}$C NMR (300 MHz, Benzene-$d_6$) δ 21.0 ($CH_2$), 22.0 (2$CH_2$), 25.1 (2$CH_2$), 29.7 ($CH_3$), 123.8 (O—C—N), 168.5 (C=O). UV/vis (MeOH): $\lambda_{max}$=667 nm. IR (KBr): ν=1750 $cm^{-1}$ (C=O), 1561 $cm^{-1}$ (N=O).

EXAMPLE 2

1-Nitroso-1-para-nitrobenzoxycyclohexane

A solution of cyclohexanone oxime (2.66 g, 23.51 mmol) in methylene chloride (50 mL) was added dropwise with stirring to a solution of LTA (10.42 g, 23.51 mmol) and 4-nitrobenzoic acid (39.29 g, 235.1 mmol) in methylene chloride (300 mL) at 0° C. A blue color gradually appeared with the addition of the oxime. After 1 h at 0. ° C., the reaction mixture was warmed to room temperature. After 3 h at room temperature, water (50 mL) was added and the organic layer was extracted with water (2×50 mL) and 3% sodium bicarbonate solution (2×50 mL). The organic layer was dried over $Na_2SO_4$, the solvent evaporated and the residue was recrystallized in diethyl ether/petroleum ether (1:1) in a −5° C. freezer to give 1-Nitroso-1-para-nitrobenzoxycyclohexane as bright blue crystals (20-25% yield): $R_f$ 0.55 (pentane/ethyl acetate=20:1); $^1$H NMR (300 MHz, Benzene-$d_6$) δ 1.17-2.04 (m, 10H), 7.38-7.98 (d, 4H); $^{13}$C NMR (300 MHz, Benzene-$d_6$) δ 22.1 (2$CH_2$), 25.0 ($CH_2$), 29.7 (2$CH_2$), 123.8 (2Ph-CH), 125.3 (O—C—N), 131.1 (2Ph-CH), 135.3 (Ph-C), 151.1 (Ph-C), 162.6 (C=O).

EXAMPLE 3

1-Nitroso-1-para-nitrobenzoxypropane

A solution of cyclohexanone oxime (3.11 g, 42.58 mmol) in methylene chloride (50 mL) was added dropwise with stirring to a solution of LTA (18.88 g, 42.58 mmol) and 4-nitrobenzoic acid (71.16 g, 425.8 mmol) in methylene chloride (300 mL) at 0° C. A blue color gradually appeared with the addition of the oxime. After 1 h at 0° C., the reaction mixture was warmed to room temperature. After 3 h at room temperature, water (50 mL) was added and the organic layer was extracted with water (2×50 mL) and 3% sodium bicarbonate solution (2×50 mL). The organic layer was dried over $Na_2SO_4$, the solvent evaporated and the residue was recrystallized in diethyl ether/petroleum ether (1:1) in a −5° C. freezer to give 1-Nitroso-1-para-nitrobenzoxypropane as bright blue crystals (25-30% yield): $R_f$ 0.5 (pentane/ethyl acetate=20:1); $^1$H NMR (300 MHz, $CDCl_3$) δ 1.69 (s, 6H), 8.31-8.48 (d, 4H); $^{13}$C NMR (300 MHz, $CDCl_3$) δ 21.1 (2$CH_3$), 122.6 (O—C—N), 124.0 (2Ph-CH), 131.4 (2Ph-CH), 135.6 (Ph-C), 151.2 (Ph-C), 162.9 (C=O).

EXAMPLE 4

1-Nitroso-1-trifluoroacetoxycyclohexane

A solution of cyclohexanone oxime (4.88 g, 43.16 mmol) in methylene chloride (50 mL) was added dropwise with stirring to a solution of LTA (19.14 g, 43.16 mmol) and trifluoroacetic acid (49.22 g, 431.6 mmol) in methylene chloride (200 mL) at 0° C. A blue color gradually appeared with the addition of the oxime After 1 h at 0° C., the reaction mixture was warmed to room temperature. After 3 h at room temperature, water (50 mL) was added and the organic layer was extracted with water (2×50 mL). The organic layer was dried over $Na_2SO_4$, the solvent evaporated and the residue was purified by column chromatography to give 1-Nitroso-1-trifluoroacetoxycyclohexane as a bright blue liquid (30% yield): $R_f$ 0.57 (pentane); $^1$H NMR (300 MHz, Benzene-$d_6$) δ 1.1-1.9 (m, 10H); $^{13}$C NMR (300 MHz, Benzene-$d_6$) δ 19.9 (2$CH_2$), 22.9 ($CH_2$), 27.4 (2$CH_2$), 113.8 (q, J=286.2 Hz), 127.2 (O—C—N), 153.7 (q, J=42.5 Hz); $^{19}$F NMR (300 MHz, Benzene-$d_6$) δ −75.7 ($CF_3$).

EXAMPLE 5

1-Nitroso-1-ortho-Acylbenzoxypropane

A solution of acetone oxime (4.03 g, 55.12 mmol) in methylene chloride (50 mL) was added dropwise with stirring to a solution of LTA (24.44 g, 55.12 mmol) and aspirin (99.0 g, 551.2 mmol) in methylene chloride (500 mL) at 0° C. A blue color gradually appeared with the addition of the oxime. After 1 h at 0° C., the reaction mixture was warmed to room temperature. After 3 h, the reaction mixture was filtered and the filtrate was extracted with water (3×100 mL). The organic layer was dried over $Na_2SO_4$, the solvent evaporated and the residue was purified by column chromatography to give the 1-Nitroso-1-ortho-Acylbenzoxypropane as a blue solid. (10% yield): $R_f$ 0.45 (pentane/ethyl acetate=10:1); UV/vis (MeOH): $\lambda_{max}$=659 nm; IR (KBr): $\nu_{C=O}$=1768 $cm^{-1}$, $\nu_{C=O}$=1731 $cm^{-1}$, $\nu_{N=O}$=1572 $cm^{-1}$; $^1$H NMR (300 MHz, Benzene-$d_6$): δ 1.2 (s, 6H), 2.0 (s, 3H), 6.91-6.99 (m, 2H), 7.11-7.17 (dd, 1H, J1=7.7 Hz, J2=1.7 Hz), 8.13-8.16 (m, 1H); $^{13}$C NMR (300 MHz, Benzene-$d_6$): δ 20.6 (2$CH_3$), 25.4 ($CH_3$), 121.8 (O—C—N), 124.0 (Ph-C), 124.5 (Ph-CH), 126.3 (Ph-CH), 132.1 (Ph-CH), 134.6 (Ph-CH), 151.9 (Ph-C), 163.0 (C=O), 169.2 (C=O).

EXAMPLE 6

General Example of Using (Diacetoxyiodo) Benzene as Oxidants (Diacetoxyiodo) benzene (1.2 mol equivalents) was added to a solution of oxime (1 mol equivalent) in methylene chloride at 0° C. under argon with stirring. After 2 hour, the reaction mixture was poured into a saturated aqueous solution of sodium bicarbonate. The layers were separated and the aqueous layer was re-extracted with methylene chloride. The organic layers were combined, dried over magnesium sulfate, filtered and concentrated to give a blue acyloxy nitroso compound that can be purified by flash chromatography or in some cases distillation or recrystallization. Individual reactions might require variations, which are apparent to those skilled in the art based upon the general example.

EXAMPLE 7

General Example of Preparing Acyloxy Nitroso Compounds by Acylation of the Anion of a Nitro Compound Followed by a [3, 2] Sigmatropic Rearrangement A nitro compound (1 mol equivalent) would be added slowly to a suspension of potassium t-butoxide (1 mol equivalent) in dry diethyl ether under argon at 0° C. with stirring. After 30 min, acetic anhydride (1 mol equivalent) was added slowly over 25 minutes and the mixture was stirred. After 2 h, the mixture was filtered and the precipitate was washed with diethyl ether until the diethyl ether was colorless. The blue filtrate was concentrated to give a blue oil that was purified by either flash chromatography, distillation or recrystallization. Individual reactions might require variations, which are apparent to those skilled in the art based upon the general example.

The foregoing is illustrative of the present invention, and is not to be construed as limiting thereof. The invention is defined by the following claims, with equivalents of the claims to be included therein.

That which is claimed is:

1. A pharmaceutical composition for treating congestive heart failure, comprising, in combination, a pharmaceutically acceptable carrier and a treatment effective amount of a compound of Formula (III):

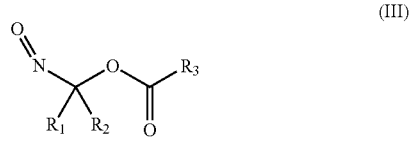

(III)

wherein:
R$_1$ is C1-C4 alkyl and R$_2$ is selected from the group consisting of CCl$_3$, CH$_2$F, CHF$_2$, CF$_3$, CH$_2$CF$_3$, CF$_2$CF$_3$, CH$_2$CF$_2$CF$_3$, CH$_2$CH$_2$CF$_3$, CF$_2$CF$_2$CF$_3$, CH$_2$CH$_2$CH$_2$CF$_3$CH$_2$CH$_2$CF$_2$CF$_3$, CH$_2$CF$_2$CF$_2$CF$_3$, and CF$_2$CF$_2$CF$_2$CF$_3$;

or R$_1$ is selected from the group consisting of CCl$_3$, CH$_2$F, CHF$_2$, CF$_3$, CH$_2$CF$_3$, CF$_2$CF$_3$, CH$_2$CF$_2$CF$_3$, CH$_2$CH$_2$CF$_3$, CF$_2$CF$_2$CF$_3$, CH$_2$CH$_2$CH$_2$CF$_3$, CH$_2$CH$_2$CF$_2$CF$_3$,CH$_2$CF$_2$CF$_2$CF$_3$, and CF$_2$CF$_2$CF$_2$CF$_3$ and R$_2$ is C1-C4 alkyl;

or R$_1$ and R$_2$ are each independently selected from the group consisting of CCl$_3$, CH$_2$F, CHF$_2$, CF$_3$, CH$_2$CF$_3$, CF$_2$CF$_3$, CH$_2$CF$_2$CF$_3$, CH$_2$CH$_2$CF$_3$, CF$_2$CF$_2$CF$_3$, CH$_2$CH$_2$CH$_2$CF$_3$, CH$_2$CH$_2$CF$_2$CF$_3$, CH$_2$CF$_2$CF$_2$CF$_3$, and CF$_2$CF$_2$CF$_2$CF$_3$;

or R$_1$ and R$_2$ together form a C2-C7 alkylene chain; and R$_3$ is selected from the group consisting of CCl$_3$, CH$_2$F, CHF$_2$, CH$_2$CF$_3$,CF$_2$CF$_3$, CH$_2$CH$_2$CF$_3$, CH$_2$CF$_2$CF$_3$, CF$_2$CF$_2$CF$_3$, CH$_2$CH$_2$CH$_2$CF$_3$, CH$_2$CH$_2$CF$_2$CF$_3$, CH$_2$CF$_2$CF$_2$CF$_3$, CF$_2$CF$_2$CF$_2$CF$_3$, CH$_2$CH$_2$CH$_2$CH$_2$CF$_3$, CH$_2$CH$_2$CH$_2$CF$_2$CF$_3$, CH$_2$CH$_2$CF$_2$CF$_2$CF$_3$, CH$_2$CF$_2$CF$_2$CF$_2$CF$_3$, and CF$_2$CF$_2$CF$_2$CF$_2$CF$_3$;

or a pharmaceutically acceptable salt or prodrug thereof.

2. The composition of claim 1, wherein said cardiovascular disorder is congestive heart failure.

3. The composition of claim 1 wherein said composition is an injectable composition.

4. The composition of claim 1 wherein said composition is tablet or capsule.

5. The composition of claim 1, wherein said compound is selected from the group consisting of

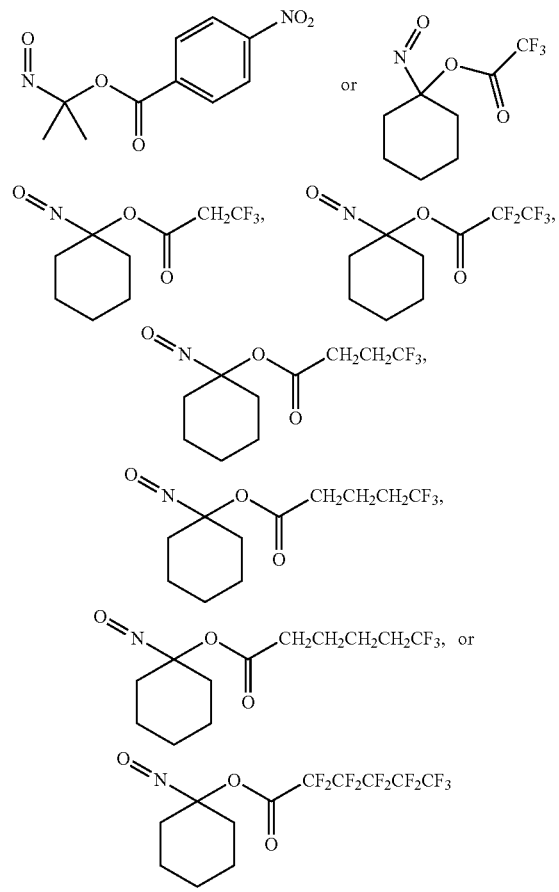

or a pharmaceutically acceptable salt or prodrug thereof.

6. A method of treating congestive heart failure in a subject in need thereof, comprising administering said subject a treatment effective amount of a compound of Formula (III):

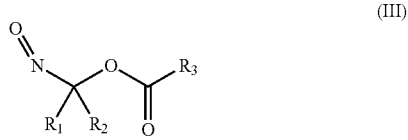

(III)

wherein:
R$_1$ is C1-C4 alkyl and R$_2$ is selected from the group consisting of CCl$_3$, CH$_2$F, CHF$_2$, CF$_3$, CH$_2$CF$_3$, CF$_2$CF$_3$, CH$_2$CF$_2$CF$_3$, CH$_2$CH$_2$CF$_3$, CF$_2$CF$_2$CF$_3$, CH$_2$CH$_2$CH$_2$CF$_3$, CH$_2$CH$_2$CF$_2$CF$_3$, CH$_2$CF$_2$CF$_2$CF$_3$, and CF$_2$CF$_2$CF$_2$CF$_3$;

or R$_1$ is selected from the group consisting of CCl$_3$, CH$_2$F, CHF$_2$, CF$_3$, CH$_2$CF$_3$, CF$_2$CF$_3$, CH$_2$CF$_2$CF$_3$, CH$_2$CH$_2$CF$_3$, CF$_2$CF$_2$CF$_3$, CH$_2$CH$_2$CH$_2$CF$_3$, CH$_2$CH$_2$CF$_2$CF$_3$, CH$_2$CF$_2$CF$_2$CF$_3$, and CF$_2$CF$_2$CF$_2$CF$_3$ and R$_2$ is C1-C4 alkyl;

or R$_1$ and R$_2$ are each independently selected from the group consisting of CCl$_3$, CH$_2$F, CHF$_2$, CF$_3$, CH$_2$CF$_3$, CF$_2$CF$_3$, CH$_2$CF$_2$CF$_3$, CH$_2$CH$_2$CF$_3$, CF$_2$CF$_2$CF$_3$, CH$_2$CH$_2$CH$_2$CF$_3$, CH$_2$CH$_2$CF$_2$CF$_3$, CH$_2$CF$_2$CF$_2$CF$_3$, and CF$_2$CF$_2$CF$_2$CF$_3$;

or R$_1$ and R$_2$ together form a C2-C7 alkylene chain; and

R$_3$ is selected from the group consisting of CCl$_3$, CH$_2$F, CHF$_2$, CH$_2$CF$_3$, CF$_2$CF$_3$, CH$_2$CH$_2$CF$_3$, CH$_2$CF$_2$CF$_3$, CF$_2$CF$_2$CF$_3$, CH$_2$CH$_2$CH$_2$CF$_3$, CH$_2$CH$_2$CF$_2$CF$_3$, CH$_2$CF$_2$CF$_2$CF$_3$, CF$_2$CF$_2$CF$_2$CF$_3$, CH$_2$CH$_2$CH$_2$CH$_2$CF$_3$, CH$_2$CH$_2$CH$_2$CF$_2$CF$_3$, CH$_2$CH$_2$CF$_2$CF$_2$CF$_3$, CH$_2$CF$_2$CF$_2$CF$_2$CF$_3$, and CF$_2$CF$_2$CF$_2$CF$_2$CF$_3$;

or a pharmaceutically acceptable salt or prodrug thereof.

7. The method of claim 6, further comprising concurrently administering a beta blocker to said subject in a treatment effective amount.

8. The method of claim 6, wherein said compound is selected from the group consisting of:

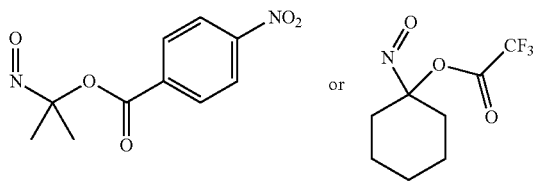

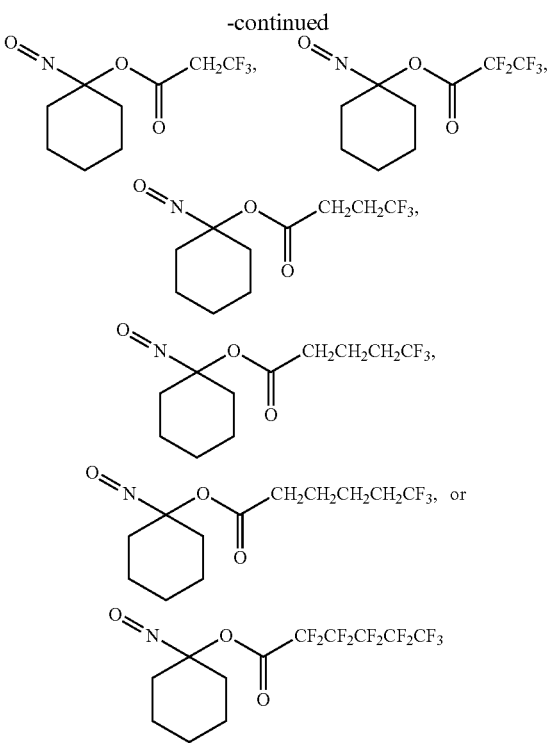

or a pharmaceutically acceptable salt or prodrug thereof.

9. The method of claim 6 wherein said congestive heart failure is caused by coronary artery disease, myocardial infarction, high blood pressure, heart valve disease, congenital heart defects, endocarditis, myocarditis, or any combination thereof.

10. The method of claim 6, wherein said administering step is carried out by parenteral injection or oral administration.

* * * * *

UNITED STATES PATENT AND TRADEMARK OFFICE
CERTIFICATE OF CORRECTION

PATENT NO.        : 8,569,536 B2                                    Page 1 of 2
APPLICATION NO.   : 13/589422
DATED             : October 29, 2013
INVENTOR(S)       : King It is certified that error appears in the above-identified patent and that said Letters Patent is hereby corrected as shown below:

In the Claims:

Column 15, Claim 1, Line 51: Please correct "of CCI$_3$,"
to read -- of CCl$_3$, --

Column 15, Claim 1, Line 53: Please correct "CH$_2$CH$_2$CH$_2$CF$_3$CH$_2$CH$_2$CF$_2$CF$_3$,"
to read -- CH$_2$CH$_2$CH$_2$CF$_3$, CH$_2$CH$_2$CF$_2$CF$_3$, --

Column 15, Claim 1, Line 55: Please correct "of CCI$_3$,"
to read -- of CCl$_3$, --

Column 15, Claim 1, Line 58: Please correct "CH$_2$CH$_2$CF$_2$CF$_3$,CH$_2$CF$_2$CF$_2$CF$_3$,"
to read -- CH$_2$CH$_2$CF$_2$CF$_3$, CH$_2$CF$_2$CF$_2$CF$_3$, --

Column 15, Claim 1, Line 61; Please correct "of CCI$_3$,"
to read -- of CCl$_3$, --

Column 15, Claim 1, Line 66: Please correct "of CCI$_3$,"
to read -- of CCl$_3$, --

Column 15, Claim 1, Line 67: Please correct "CH$_2$CF$_3$,CF$_2$CF$_3$,"
to read -- CH$_2$CF$_3$, CF$_2$CF$_3$, --

Column 16, Claim 6, Line 67: Please correct "of CCI$_3$,"
to read -- of CCl$_3$, --

Column 17, Claim 6, Line 4: Please correct "of CCI$_3$,"
to read -- of CCl$_3$, --

Signed and Sealed this
Fifteenth Day of April, 2014

Michelle K. Lee
*Deputy Director of the United States Patent and Trademark Office*

CERTIFICATE OF CORRECTION (continued)
U.S. Pat. No. 8,569,536 B2

Column 17, Claim 6, Line 6: Please correct "$CH_2CH_2CF_3,CF_2CF_2CF_3,$"
to read -- $CH_2CH_2CF_3, CF_2CF_2CF_3,$ --

Column 17, Claim 6, Line 10: Please correct "of $CCl_3,$"
to read -- of $CCl_3,$ --

Column 17, Claim 6, Line 16: Please correct "of $CCl_3,CH_2F$"
to read -- of $CCl_3, CH_2F,$ --

UNITED STATES PATENT AND TRADEMARK OFFICE
CERTIFICATE OF CORRECTION

PATENT NO. : 8,569,536 B2  
APPLICATION NO. : 13/589422  
DATED : October 29, 2013  
INVENTOR(S) : S. Bruce King Page 1 of 1

It is certified that error appears in the above-identified patent and that said Letters Patent is hereby corrected as shown below:

In the Specification

Column 1, Line 26: Please correct "HL62198" to read --HL062198--

Signed and Sealed this
Eleventh Day of March, 2025

Coke Morgan Stewart
*Acting Director of the United States Patent and Trademark Office*